(12) United States Patent
Kino et al.

(10) Patent No.: US 8,541,209 B2
(45) Date of Patent: Sep. 24, 2013

(54) L-PROLINE CIS-4-HYDROXYLASE AND USE THEREOF TO PRODUCE CIS-4-HYDROXY-L-PROLINE

(75) Inventors: Kuniki Kino, Tokyo (JP); Ryotaro Hara, Tokyo (JP)

(73) Assignee: Kyowa Hakko Bio Co., Ltd., Tokyo (JP)

( * ) Notice: Subject to any disclaimer, the term of this patent is extended or adjusted under 35 U.S.C. 154(b) by 246 days.

(21) Appl. No.: 12/992,417

(22) PCT Filed: May 12, 2009

(86) PCT No.: PCT/JP2009/058808
§ 371 (c)(1), (2), (4) Date: Nov. 12, 2010

(87) PCT Pub. No.: WO2009/139365
PCT Pub. Date: Nov. 19, 2009

(65) Prior Publication Data
US 2011/0091942 A1 Apr. 21, 2011

(30) Foreign Application Priority Data
May 12, 2008 (JP) ................................ 2008-125213

(51) Int. Cl.
*C12P 13/24* (2006.01)

(52) U.S. Cl.
USPC ...................................................... 435/107

(58) Field of Classification Search
None
See application file for complete search history.

(56) References Cited

FOREIGN PATENT DOCUMENTS

| JP | 05-111387 A | 5/1993 |
|---|---|---|
| JP | 05-111388 A | 5/1993 |
| JP | 3005085 B2 | 1/2000 |
| JP | 3005086 B2 | 1/2000 |
| JP | 2005-112761 A | 4/2005 |

OTHER PUBLICATIONS

Wishart et al, A single mutation converts a novel phosphotyrosine binding domain into a dual-specificity phosphatase. J Biol Chem. Nov. 10, 1995;270(45):26782-26785.*
Whisstock et al, Prediction of protein function from protein sequence and structure. Q Rev Biophys. Aug. 2003;36(3):307-40. Review.*
EMBL-EBI/ENA database Acc# BAB52605 from Kaneko et al, DNA Res. Dec. 31, 2000;7(6):331-8. Complete genome structure of the nitrogen-fixing symbiotic bacterium *Mesorhizobium loti*. Alignment with SEQ ID No. 1.*
Brent et al, 1987 Chapter 16. pp. 16.0.1-18.0.5 Protein Expression. In: Current protocols in molecular biology. John Wiley & Sons, Inc. New York, NY.*
UniProtKB Acc# Q989T9 (SEQ ID No. 1) version 30. Sep. 1, 2009.*
UniProtKB Acc# Q92LF6 (SEQ ID No. 2) version 33. Sep. 1, 2009.*
Capela et al., *Proc. Natl. Acad. Sci. U.S.A.*, 98(17): 9877-9882 (Aug. 14, 2001).
Capela et al., *DATABASE UniProt*, Accession No. Q92LF6 (Dec. 1, 2001).
Kaneko et al., *DNA Research*, 7: 331-338 (2000).
Kaneko et al., *DATABASE UniProt*, Accession No. Q989T9 (Oct. 1, 2001).
European Patent Office, Extended European Search Report for European Application No. 09746572.8 (Oct. 10, 2011).
Capela et al., Database DDBJ/EMBL/GenBank [Online], Accession No. AL591688 (May 6, 2008).
Capela et al., Database DDBJ/EMBL/GenBank [Online], Accession No. CAC47686 (May 6, 2008).
Hara et al., Biochemical and Biophysical Research Communications, 379(4): 882-886 (Feb. 20, 2009).
Kaneko et al., Database DDBJ/EMBL/GenBank [Online], Accession No. BA000012 (May 19, 2007).
Kaneko et al., Database DDBJ/EMBL/GenBank [Online], Accession No. BAB52605 (May 19, 2007).
Shibasaki et al., Journal of Bioscience and Bioengineering, 90(5): 522-525 (2000).
Japanese Patent Office, International Search Report in International Application No. PCT/JP2009/058808 (Jun. 9, 2009), English translation.
Japanese Patent Office, International Preliminary Report on Patentability in International Application No. PCT/JP2009/058808 (Apr. 23, 2010), English translation.

* cited by examiner

*Primary Examiner* — Sheridan Swope
(74) *Attorney, Agent, or Firm* — Leydig, Voit & Mayer, Ltd.

(57) ABSTRACT

Development of a method of economically and efficiently producing cis-4-hydroxy-L-proline. The present invention provides L-proline cis-4-hydroxylase. This enzyme may be derived from *Lotus corniculatus rhizobia*, *Mesorhizobium loti* or *Medicago sativa rhizobia*, *Sinorhizobium meliloti*. The present invention provides a method of producing cis-4-hydroxy-L-proline from L-proline by using this enzyme. The present invention provides a recombinant vector containing a polynucleotide encoding the enzyme and a transformant containing the vector.

4 Claims, 13 Drawing Sheets recombinant plasmid map

FIG. 2 procedures for derivatization of amino acid reaction solution 200 μl
   ↓← 30% trichloroacetic acid 50 μl
stirring
  ↓
centrifugation (20000 × g, 4°C, 10 min)
  ↓
supernatant 100 μl
   ← 0.5 M boric acid・NaOH buffer (pH9.0) 50 μl
   ← 5 M NaOH 9 μl
   ↓← 15 mM Marfey's reagent 50 μl
40°C, 1 hr, stirring in shading
   ↓← 1 M HCl 50 μl
filtration (0.45 μm filter)
  ↓
HPLC analysis

FIG. 7 ion exchange column (Oasis HLB)

↓ ← 100% CH₃OH 3 ml (equilibration)

↓ ← H₂O 3 ml (equilibration)

↓ ← HPLC analysis sample 1 ml

↓ ← 5% CH₃OH 5 ml (washing)

↓ ← 2% NH₄OH 4 ml (elution)

drying to solidness under reduced pressure

↓ ← 100% CH₃OH 1 ml filtration (0.45 μm filter)

↓

MS analysis

MS analyses of resulting products
(upper panel: BAB52605, lower panel: CAC47686)

MS/MS/MS analyses of resulting products
(upper panel: BAB52605, middle panel: CAC47686, lower panel: cis-4Hyp)

SEQUENCE LISTING

<160> NUMBER OF SEQ ID NOS: 8

<210> SEQ ID NO 1
<211> LENGTH: 280
<212> TYPE: PRT
<213> ORGANISM: Mesorhizobium loti MAFF303099

<400> SEQUENCE: 1

Met Thr Thr Arg Ile Leu Gly Val Val Gln Leu Asp Gln Arg Arg Leu
1               5                   10                  15

Thr Asp Asp Leu Ala Val Leu Ala Lys Ser Asn Phe Ser Glu Tyr
            20                  25                  30

Ser Asp Phe Ala Cys Gly Arg Trp Glu Phe Cys Met Leu Arg Asn Gln
            35                  40                  45

Ser Gly Lys Gln Glu Glu Gln Arg Val Val His Glu Thr Pro Ala
        50                  55                  60

Leu Ala Thr Pro Leu Gly Gln Ser Leu Pro Tyr Leu Asn Glu Leu Leu
65                  70                  75                  80

Asp Asn His Phe Asp Arg Asp Ser Ile Arg Tyr Ala Arg Ile Ile Arg
                85                  90                  95

Ile Ser Glu Asn Ala Cys Ile Ile Pro His Arg Asp Tyr Leu Glu Leu
            100                 105                 110

Glu Gly Lys Phe Ile Arg Val His Leu Val Leu Asp Thr Asn Glu Lys
        115                 120                 125

Cys Ser Asn Thr Glu Glu Asn Asn Ile Phe His Met Gly Arg Gly Glu
130                 135                 140

Ile Trp Phe Leu Asp Ala Ser Leu Pro His Ser Ala Gly Cys Phe Ser
145                 150                 155                 160

Pro Thr Pro Arg Leu His Leu Val Val Asp Ile Gly Thr Arg Ser
                165                 170                 175

Leu Glu Glu Val Ala Ile Asn Val Glu Gln Pro Ser Ala Arg Asn Ala
            180                 185                 190

Thr Val Asp Thr Arg Lys Glu Trp Thr Asp Glu Thr Leu Glu Ser Val
        195                 200                 205

Leu Gly Phe Ser Glu Ile Ile Ser Glu Ala Asn Tyr Arg Glu Ile Val
    210                 215                 220

Ala Ile Leu Ala Lys Leu His Phe Phe His Lys Val His Cys Val Asp
225                 230                 235                 240

Met Tyr Gly Trp Leu Lys Glu Ile Cys Arg Arg Arg Gly Glu Pro Ala
                245                 250                 255

Leu Ile Glu Lys Ala Asn Ser Leu Glu Arg Phe Tyr Leu Ile Asp Arg
            260                 265                 270

Ala Ala Gly Glu Val Met Thr Tyr
        275                 280

<210> SEQ ID NO 2
<211> LENGTH: 280
<212> TYPE: PRT
<213> ORGANISM: Sinorhizobium meliloti 1021

<400> SEQUENCE: 2

Met Ser Thr His Phe Leu Gly Lys Val Lys Phe Asp Glu Ala Arg Leu
1               5                   10                  15

Ala Glu Asp Leu Ser Thr Leu Gly Val Ala Glu Phe Ser Ser Ala Tyr
            20                  25                  30

```
Ser Asp Phe Ala Cys Gly Lys Trp Glu Ala Cys Val Leu Arg Asn Arg
         35                  40                  45

Thr Gly Met Gln Glu Glu Asp Ile Val Val Ser His Asn Ala Pro Ala
 50                  55                  60

Leu Ala Thr Pro Leu Ser Lys Ser Leu Pro Tyr Leu Asn Glu Leu Val
 65                  70                  75                  80

Glu Thr His Phe Asp Cys Ser Ala Val Arg Tyr Thr Arg Ile Val Arg
                 85                  90                  95

Val Ser Glu Asn Ala Cys Ile Ile Pro His Ser Asp Tyr Leu Glu Leu
                100                 105                 110

Asp Glu Thr Phe Thr Arg Leu His Leu Val Leu Asp Thr Asn Ser Gly
                115                 120                 125

Cys Ala Asn Thr Glu Glu Asp Lys Ile Phe His Met Gly Leu Gly Glu
130                 135                 140

Ile Trp Phe Leu Asp Ala Met Leu Pro His Ser Ala Ala Cys Phe Ser
145                 150                 155                 160

Lys Thr Pro Arg Leu His Leu Met Ile Asp Phe Glu Ala Thr Ala Phe
                165                 170                 175

Pro Glu Ser Phe Leu Arg Asn Val Glu Gln Pro Val Thr Thr Arg Asp
                180                 185                 190

Met Val Asp Pro Arg Lys Glu Leu Thr Asp Glu Val Ile Glu Gly Ile
                195                 200                 205

Leu Gly Phe Ser Ile Ile Ile Ser Glu Ala Asn Tyr Arg Glu Ile Val
210                 215                 220

Ser Ile Leu Ala Lys Leu His Phe Phe Tyr Lys Ala Asp Cys Arg Ser
225                 230                 235                 240

Met Tyr Asp Trp Leu Lys Glu Ile Cys Lys Arg Arg Gly Asp Pro Ala
                245                 250                 255

Leu Ile Glu Lys Thr Ala Ser Leu Glu Arg Phe Phe Leu Gly His Arg
                260                 265                 270

Glu Arg Gly Glu Val Met Thr Tyr
                275                 280

<210> SEQ ID NO 3
<211> LENGTH: 843
<212> TYPE: DNA
<213> ORGANISM: Mesorhizobium loti MAFF303099

<400> SEQUENCE: 3
atgacaacgc ggatattggg tgtggtccag cttgatcaaa ggcgactgac agacgatttg      60
gctgtcttag cgaagtccaa cttctcgagc gaatattcgg atttcgcctg cgggcggtgg     120
gaattctgca tgctccgcaa tcagtcgggg aagcaggagg agcagagagt ggtcgtccac     180 gagacccag cgctggcgac acctctgggc aatccttac cctatctcaa tgaattgttg     240
gacaatcact tgataggga ctctatacgc tacgcgcgga tcatccggat atcagaaaac     300
gcgtgtataa taccctcaccg tgattacttg gaactagaag ggaaatttat cagagtgcac     360
ctagttctag atacgaatga aaagtgttcc aatacagaag agaataatat attccatatg     420
ggacgaggtg agatctggtt tcttgacgca agcctgccgc acagcgcggg atgtttctca     480
ccaactccac gcttacatct agtggtcgac atcgagggga ctcgttccct ggaagaggtt     540
gcaatcaatg tcgaacagcc gtcggcaagg aatgccacgg tggatactcg caaggagtgg     600
actgatgaaa cgctcgaatc cgttctggga ttttcggaga ttatcagcga ggccaattat     660
cgagagatcg tcgcgattct ggcgaagctc cacttttttcc acaaggtcca ctgcgtggat     720
```

```
atgtatggct ggcttaagga aatctgccga cgtcgtggcg agccggcgct tatagaaaag    780
gccaactcgc ttgagcgatt ttatctcatt gaccgtgctg ctggcgaggt catgacttat    840
tga                                                                 843
```

<210> SEQ ID NO 4
<211> LENGTH: 843
<212> TYPE: DNA
<213> ORGANISM: Sinorhizobium meliloti 1021

<400> SEQUENCE: 4

```
atgagcaccc atttcttggg caaggtcaag ttcgatgaag cgcgattggc agaagatcta     60
tctaccttgg aagttgccga gttctcgagt gcatactcgg acttcgcgtg cggtaaatgg    120
gaggcatgcg tgctacgcaa tcggaccgga atgcaggagg aagatatcgt cgtaagtcac    180
aacgctcctg cactggccac gccgctgagc aagtcgctgc cgtatctgaa cgaacttgtt    240
gaaacccact tcgattgcag cgctgttcgg tatacaagaa ttgtccgtgt atcagaaaac    300
gcatgtataa tcccccatag tgattaccta gaactagatg agaccttcac aaggttacac    360
ctggtgttag acactaattc aggatgcgct aatactgagg aagataaaat atttcatatg    420
ggactgggag agatttggtt ccttgacgct atgttaccgc atagcgctgc ttgttttttcc    480 aaaactccgc gcctgcatct gatgatcgac tttgaggcta ccgctttttcc cgaatctttt    540 ctgcgaaatg tcgaacaacc agtgacaaca cgagacatgg ttgatcctcg gaaggaacta    600
accgatgagg ttatcgaagg tattctgggg ttttcaataa ttattagcga agccaattac    660
cgggaaattg tttctattct ggcgaagcta cacttcttct acaaggcaga ctgtcgatca    720
atgtacgact ggctgaagga aatctgcaaa cgtcgagggg atcctgcact tattgaaaag    780
accgcctcgc tcgagcgatt ttttctaggg caccgtgaac gtggcgaggt gatgacatac    840
taa                                                                 843
```

<210> SEQ ID NO 5
<211> LENGTH: 37
<212> TYPE: DNA
<213> ORGANISM: Artificial Sequence
<220> FEATURE:
<223> OTHER INFORMATION: Synthetic Sequence
<400> SEQUENCE: 5

```
tgaatatacc atggcaacgc ggatattggg tgtggtc                              37
```

<210> SEQ ID NO 6
<211> LENGTH: 40
<212> TYPE: DNA
<213> ORGANISM: Artificial Sequence
<220> FEATURE:
<223> OTHER INFORMATION: Synthetic Sequence
<400> SEQUENCE: 6

```
atgaattcaa gcttataagt catgacctcg ccagcagcac                           40
```

<210> SEQ ID NO 7
<211> LENGTH: 35
<212> TYPE: DNA
<213> ORGANISM: Artificial Sequence
<220> FEATURE:
<223> OTHER INFORMATION: Synthetic Sequence
<400> SEQUENCE: 7

```
tgaatatacc atgggcaccc atttcttggg caagg                                35
```

```
<210> SEQ ID NO 8
<211> LENGTH: 38
<212> TYPE: DNA
<213> ORGANISM: Artificial Sequence
<220> FEATURE:
<223> OTHER INFORMATION: Synthetic Sequence

<400> SEQUENCE: 8
atgaattcaa gcttgtatgt catcacctcg ccacgttc                              38
```

L-PROLINE CIS-4-HYDROXYLASE AND USE THEREOF TO PRODUCE CIS-4-HYDROXY-L-PROLINE

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 8,330 bytes ASCII (Text) file named "707223 SequenceListing.txt," created Nov. 11, 2010.

TECHNICAL FIELD

The present invention relates to L-proline cis-4-hydroxylase enzyme, a production method of cis-4-hydroxy-L-proline using the enzyme, a recombinant vector containing a polynucleotide encoding the aforementioned enzyme, and a transformant containing the recombinant vector.

BACKGROUND ART

Hydroxy-L-proline is one kind of modified amino acids having a structure wherein a hydroxyl group is introduced into L-proline. It has 4 kinds of isomers due to the difference in the site into which the hydroxyl group is introduced (the 3-position or the 4-position carbon atom), and the difference in the spatial configuration of the hydroxyl group (trans configuration or cis configuration). Among the isomers of hydroxyproline, cis-4-hydroxy-L-proline is a substance useful as a starting material of a synthetic intermediate for pharmaceutical products such as carbapenem antibiotic, N-acetylhydroxyproline utilized as an anti-inflammatory agent and the like.

As a production method of cis-4-hydroxy-L-proline, a method of organic synthesis of a cis-4-hydroxy-L-proline derivative from a trans-4-hydroxy-L-proline derivative has been proposed (patent document 1). However, it has a problem in that a trans-4-hydroxy-L-proline derivative, which is the synthesis starting material, itself is expensive. While methods of producing cis-4-hydroxy-L-proline from L-proline by using microorganisms such as the genus *Helicoceras* and the like have also been proposed (patent documents 2 and 3), the production amount is extremely as low as 0.65 g/L, and is not practical.

patent document 1: JP-A-2005-112761
patent document 2: JP-B-3005085
patent document 3: JP-B-3005086

DISCLOSURE OF THE INVENTION

Problems to be Solved by the Invention

There is a need to develop a method of economically and efficiently producing industrially useful cis-4-hydroxy-L-proline.

Means of Solving the Problems

The present invention provides L-proline cis-4-hydroxylase. The L-proline cis-4-hydroxylase of the present invention may be selected from the group consisting of ((1) a protein consisting of the amino acid sequence of SEQ ID NO: 1 or 2, (2) a protein consisting of an amino acid sequence wherein one or several amino acids is/are deleted from, substituted in or added to the amino acid sequence of SEQ ID NO: 1 or 2, which has L-proline cis-4-hydroxylase activity, (3) a protein consisting of an amino acid sequence having homology of not less than 80% with the amino acid sequence of SEQ ID NO: 1 or 2, which has L-proline cis-4-hydroxylase activity, (4) a protein consisting of an amino acid sequence encoded by a polynucleotide consisting of a nucleotide sequence having homology of not less than 80% with the nucleotide sequence of SEQ ID NO: 3 or 4, which has L-proline cis-4-hydroxylase activity, (5) a protein consisting of an amino acid sequence encoded by a polynucleotide that hybridizes with a polynucleotide consisting of the nucleotide sequence of SEQ ID NO: 3 or 4 under stringent conditions, which has L-proline cis-4-hydroxylase activity, and (6) a fusion protein of any of the proteins of the aforementioned (1) to (5) and a tag peptide for specific binding attached thereto.

The present invention provides a production method of cis-4-hydroxy-L-proline. The production method of the cis-4-hydroxy-L-proline of the present invention includes a step of providing the L-proline cis-4-hydroxylase of the present invention and L-proline, and
(2) a step of reacting the aforementioned L-proline cis-4-hydroxylase with the aforementioned L-proline to give cis-4-hydroxyproline.

The present invention provides a recombinant vector containing polynucleotide encoding the L-proline cis-4-hydroxylase of the present invention.

The present invention provides a transformant containing the recombinant vector of the present invention.

In the present specification, the "protein", "peptide", "oligopeptide" and "polypeptide" are compounds wherein two or more amino acids are connected by peptide bond(s). The "protein", "peptide", "oligopeptide" and "polypeptide" may be modified by an alkyl group including methyl group, a phosphate group, a sugar chain, and/or an ester bond or other covalent bond. In addition, the "protein", "peptide", "oligopeptide" and "polypeptide" may be bound or associated with a metal ion, coenzyme, allosteric ligand, other atom, ion or atomic group, or other "protein", "peptide", "oligopeptide" or "polypeptide", or biopolymer such as sugar, lipid, nucleic acid and the like, or polystyrene, polyethylene, polyvinyl, polyester or other synthetic polymer, via a covalent bond or noncovalent bond.

When amino acid is indicated in the present specification, it may be shown by a compound name such as L-asparagine, L-glutamine and the like, or by conventionally-used 3 letters such as Asn, Gln and the like. When a compound name is used, a prefix (L- or D-) showing the steric configuration relating to a carbon of the amino acid is used therefor. When the conventional 3 letters are used, the 3 letters represent an L form of amino acid unless otherwise specified. In the present specification, amino acid is a compound bound with an amino group and a carboxyl group via at least one carbon atom, and is any compound capable of polymerizing by peptide bond. While the amino acid in the present specification includes 20 kinds of L-amino acids used for the translation of protein synthesized from messenger RNA in ribosome in vivo and D-amino acids which are stereoisomers thereof, it is not limited thereto and may include any natural or unnatural amino acid.

In the present specification, isomers of hydroxyproline (hereinafter to be referred to as "Hyp") may be indicated as trans-3-Hyp, cis-3-Hyp, trans-4-Hyp and cis-4-Hyp depending on the difference in the site where a hydroxyl group is introduced (carbon atom at the 3-position or the 4-position), and the difference in the spatial configuration of a hydroxyl group (trans configuration or cis configuration).

The structure of cis-4-hydroxy-L-proline (cis-4-Hyp) is represented by chemical formula I.

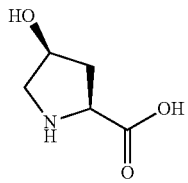

The L-proline cis-4-hydroxylase of the present invention is produced by expressing a DNA consisting of a nucleotide sequence encoding the amino acid sequence thereof in a nonliving expression system or an expression system using a host organism and an expression vector. The aforementioned host organism includes procaryotes such as *Escherichia coli, Bacillus subtilis* and the like, and eucaryotes such as yeast, fungi, plant, animal and the like. The expression system using a host organism and an expression vector of the present invention may be a part of an organism such as cell and tissue, or a whole individual organism. The enzyme protein of the present invention may be used, as long as it has L-proline cis-4-hydroxylase activity, for the production method of cis-4-Hyp of the present invention in admixture with other components derived from a nonliving expression system or expression system using a host organism and an expression vector. When the enzyme protein of the present invention is expressed in the aforementioned expression system using a host organism and an expression vector, the host organism that expresses the aforementioned enzyme protein, for example, the transformant of the present invention, which is used for the production of cis-4-Hyp of the present invention, may be in a living state. In this case, the cis-4-Hyp of the present invention can be produced by a resting microbial cell reaction system or a fermentation method. Alternatively, the aforementioned enzyme protein may be purified for use in the production method of the cis-4-Hyp of the present invention.

The amino acid sequence of SEQ ID NO: 1 and the nucleotide sequence of SEQ ID NO: 3 are the amino acid sequence of BAB52605 protein derived from *Lotus corniculatus rhizobia, Mesorhizobium loti* MAFF303099, and the nucleotide sequence of a gene encoding the BAB52605 protein, respectively. The BAB52605 protein has an ability to convert L-proline to cis-4-Hyp. The amino acid sequence of SEQ ID NO: 1 is deposited under Accession No. BAB52605 in the database GenBank. The nucleotide sequence of SEQ ID NO: 3 is deposited under Accession No. BA000012 in the database GenBank. While the BAB52605 protein was annotated as L-proline 3-hydroxylase in GenBank, the protein actually has L-proline cis-4-hydroxylase activity that produces cis-4-Hyp from proline, and does not show L-proline 3-hydroxylase activity, as shown in the Examples of the present invention.

The amino acid sequence of SEQ ID NO: 2 and the nucleotide sequence of SEQ ID NO: 4 are the amino acid sequence of CAC47686 protein derived from *Medicago saliva rhizobia, Sinorhizobium meliloti* 1021, and the nucleotide sequence of the gene encoding the CAC47686 protein. The CAC47686 protein has an ability to convert L-proline to cis-4-Hyp. The amino acid sequence of SEQ ID NO: 2 is deposited under Accession No. CAC47686 in the database GenBank/EMBL. The amino acid sequence of SEQ ID NO 4 is deposited under Accession No. AL591792 in the database GenBank.

In the present specification, the homology of the nucleotide sequence is represented by the percentage obtained by aligning the nucleotide sequence of the present invention and that of a comparison object such that the nucleotide sequences match with each other most, and dividing the number of nucleotides in the matched parts of the nucleotide sequence by the total number of the nucleotides of the nucleotide sequence of the present invention. Similarly, the homology of the amino acid sequence in the present specification is represented by the percentage obtained by aligning the amino acid sequence of the present invention and that of a comparison object such that the highest number of amino acid residues match between the amino acid sequences, and dividing the number of the matched amino acid residues by the total number of the amino acid residues of the amino acid sequence of the present invention. The homology of the nucleotide sequence and amino acid sequence of the present invention can be calculated by using an alignment program CLUSTALW well known to those of ordinary skill in the art.

In the present specification, the "stringent conditions" mean to perform Southern blotting method explained in Sambrook, J. and Russell, D. W., Molecular Cloning A Laboratory Manual 3rd Edition, Cold Spring Harbor Laboratory Press (2001) under the following experiment conditions. A polynucleotide consisting of the nucleotide sequence of the comparison object is subjected to agarose electrophoresis to allow formation of a band, and immobilized on a nitrocellulose filter or other solid phase by capillary phenomenon or electrophoresis, and prewashed with a solution of 6×SSC and 0.2% SDS. A polynucleotide comprising the nucleotide sequence of the present invention is labeled with a labeling substance such as radioisotope and the like to give a probe and a hybridization reaction of the probe with the aforementioned comparison object polynucleotide immobilized on the solid phase is performed overnight in a solution of 6×SSC and 0.2% SDS at 65° C. Thereafter, the aforementioned solid phase is washed twice each with a solution of 1×SSC and 0.1% SDS at 65° C. for 30 min and washed twice each with a solution of 0.2×SSC and 0.1% SDS at 65° C. for 30 min. Finally, the amount of the probe remaining on the aforementioned solid phase is determined by quantifying the aforementioned labeling substance. In the present specification, hybridization under the "stringent conditions" means that the amount of a probe remaining on a solid phase on which a polynucleotide consisting of the nucleotide sequence of a comparison object is immobilized is at least 25%, preferably at least 50%, more preferably at least 75%, of the amount of a probe remaining on a solid phase for a positive control experiment, on which a polynucleotide consisting of the nucleotide sequence of the present invention is immobilized.

The protein of the present invention may be selected from the group consisting of (1) a protein consisting of the amino acid sequence of SEQ ID NO: 1 or 2, (2) a protein consisting of an amino acid sequence wherein one or several amino acids is/are deleted from, substituted in or added to the amino acid sequence of SEQ ID NO: 1 or 2 SEQ ID NO: 1 or 2, which has L-proline cis-4-hydroxylase activity, (3) a protein consisting of an amino acid sequence having homology of not less than 80% with the amino acid sequence of SEQ ID NO: 1 or 2, which has L-proline cis-4-hydroxylase activity, (4) a protein consisting of an amino acid sequence encoded by a polynucleotide consisting of a nucleotide sequence having homology of not less than 80% with the nucleotide sequence of SEQ ID NO: 3 or 4, which has L-proline cis-4-hydroxylase activity, (5) a protein consisting of an amino acid sequence encoded by a polynucleotide that hybridizes with a polynucleotide consisting of the nucleotide sequence of SEQ ID NO: 3 or 4 under stringent conditions, which has L-proline cis-4-hydroxylase activity, and (6) a fusion protein of any of the proteins of the aforementioned (1) to (5) and a tag peptide for specific binding attached thereto.

The fusion protein of the present invention consists of a tag peptide for specific binding and any of the proteins of the aforementioned (1) to (5), wherein the peptide is attached to the amino terminal or carboxyl terminal of said protein.

The tag peptide for specific binding of the present invention is a polypeptide that specifically binds to other proteins, polysaccharides, glycolipids, nucleic acids, derivatives of these, resins and the like, to facilitate detection, separation or purification of expressed protein when any of the proteins of the aforementioned (1) to (5) is prepared. A ligand bound to the tag for specific binding may also be immobilized on a solid support or dissolved in a free form in an aqueous solution. Thus, since the fusion protein of the present invention specifically binds to a ligand immobilized on a solid support, other components in the expression system can be removed by washing. Thereafter, the aforementioned fusion protein can be separated from the solid support and collected by adding a ligand in a free form or changing pH, ion intensity and other conditions. The tag for specific binding of the present invention includes, but is not limited to, His tag, myc tag, HA tag, intein tag, MBP, GST and polypeptides analogous thereto. The tag for specific binding of the present invention may have any amino acid sequence as long as the fusion protein retains N-terminal amidase activity.

The L-proline cis-4-hydroxylase activity of the protein of the present invention may be evaluated by quantifying cis-4-Hyp produced by reacting the protein of the present invention with L-proline in a reaction solution of the protein of the present invention, L-proline, 2-oxoglutaric acid, divalent ferric ion and L-ascorbic acid.

The cis-4-Hyp may be quantified by using an analytical instrument well known to those of ordinary skill in the art, such as LC/MS and the like.

Step (2) of the production method of the present invention may be performed using a reaction solution of a buffer component for pH control in addition to the composition of the present invention and L-proline. HEPES is preferably used as the aforementioned buffer component, and pH may be adjusted to 7.0-7.5. Preferably, the aforementioned reaction solution may further contain 2-oxoglutaric acid involved as an electron donor in a hydroxide reaction by the protein of the present invention. The aforementioned reaction solution may further contain divalent ferric ion, L-ascorbic acid and the like.

To allow the composition of the present invention to react with L-proline in step (2) of the production method of the present invention, the reaction solution is incubated for a predetermined reaction time at a predetermined reaction temperature. In the production method of the present invention, the concentration of the composition of the present invention, L-proline, divalent ferric ion, 2-oxoglutaric acid and the like in the reaction solution, reaction solution volume, reaction time, reaction temperature or other reaction conditions may be determined by those of ordinary skill in the art in consideration of the relationship between the desired production amounts and yield of cis-4-Hyp, time, cost, facility and the like necessary for the production, and other conditions.

The cis-4-Hyp obtained by the production method of the present invention may be collected by a combination of operations well known to those of ordinary skill in the art, such as centrifugation, column chromatography, freeze-drying and the like. In addition, the cis-4-Hyp obtained by the production method of the present invention may be evaluated for the production amounts or purity by using analysis techniques well known to those of ordinary skill in the art, such as LC/MS.

In the present specification, the "recombinant vector" is a vector incorporating a polynucleotide encoding a protein having a desired function, which is used to afford expression of the protein having the desired function in the host organism.

In the present specification, the "vector" is a genetic factor used to afford replication and expression of a protein having a desired function in a host organism by incorporating a polynucleotide encoding the protein having the desired function therein and transducing same to the host organism. Examples thereof include, but are not limited to, plasmid, virus, phage, cosmid and the like. Preferably, the aforementioned vector may be a plasmid. More preferably, the aforementioned vector may be a pET-21d(+) plasmid.

The recombinant vector of the present invention may be produced by ligating a polynucleotide encoding the protein of the present invention and any vector according to a genetic engineering method well known to those of ordinary skill in the art who use restriction enzymes, DNA ligases and the like.

In the present specification, the "transformant" is an organism into which a recombinant vector incorporating a polynucleotide encoding a protein having a desired function has been transduced, and which has become capable of showing desired property relating to the protein having the desired function.

In the present specification, the "host organism" is an organism into which a recombinant vector incorporating a polynucleotide encoding a protein having a desired function is transduced for production of a transformant. The aforementioned host organism includes procaryotes such as *Escherichia coli*, *Bacillus subtilis* and the like, and eucaryotes such as yeast, fungi, plant, animal and the like. The aforementioned host organism may be *Escherichia coli*.

The transformant of the present invention is produced by transducing the recombinant vector of the present invention into any appropriate host organism. The recombinant vector may be transduced according to various methods well known to those of ordinary skill in the art, such as electroporation method forming a pore in the cellular membrane by electric stimulation, a heat shock method to be performed along with a calcium ion treatment and the like.

BRIEF DESCRIPTION OF THE DRAWINGS

FIG. 2 A conceptual diagram showing the procedures of quenching reaction in a hydroxide reaction test and derivatization of amino acid.

FIG. 7 A conceptual diagram showing procedures for preparation of an MS analysis sample.

DESCRIPTION OF EMBODIMENTS

Figure 1:
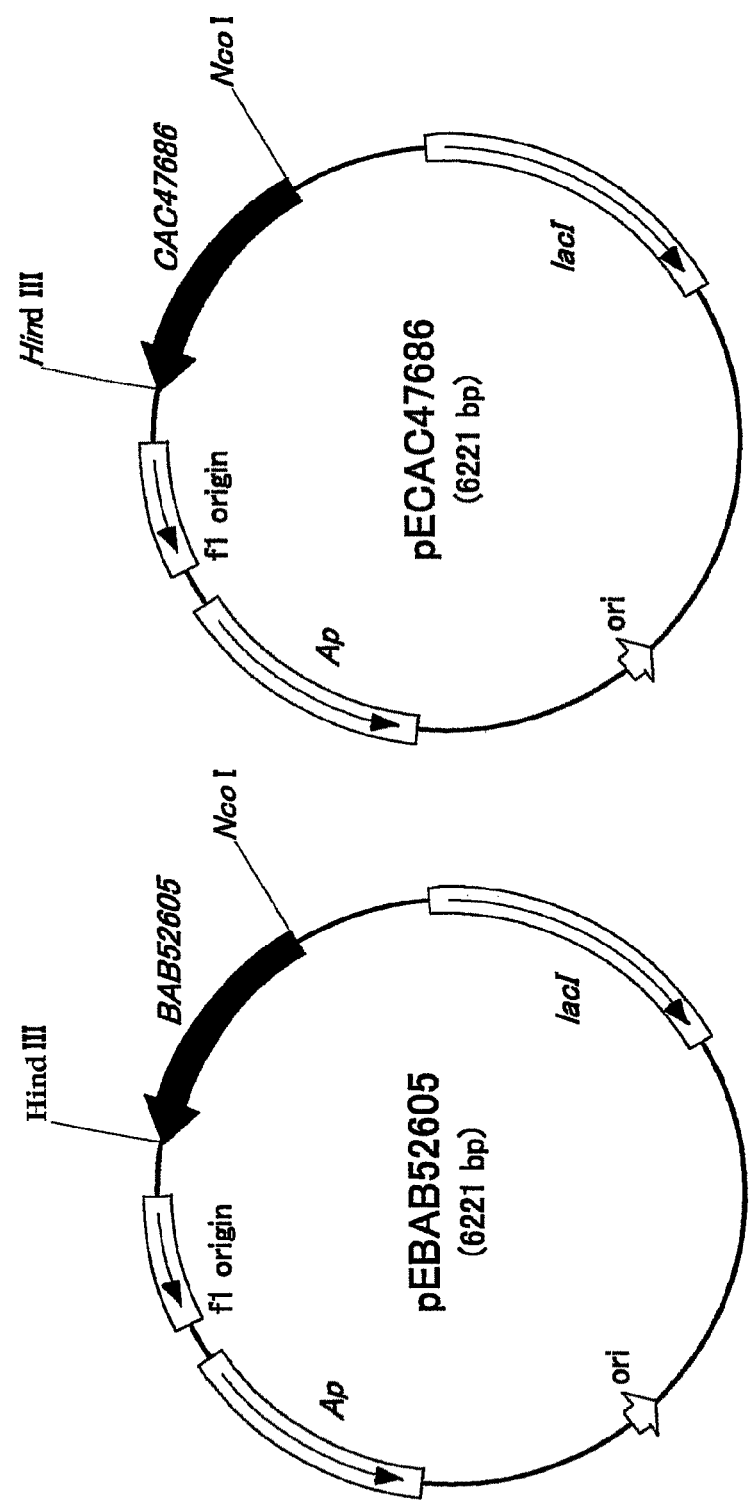
FIG. 1 Maps of recombinant plasmids.

The present invention is explained in detail in the following by referring to Examples, which are not to be construed as limitative.

Example 1

1. Cloning, Transduction and Expression of Genes Encoding Proteins BAB52605 and CAC47686

1-1. Method
(Extraction of Microorganism Chromosomal DNA to be Used as Template for Gene Amplification)

*Lotus corniculatus rhizobia, Mesorhizobium loti* MAFF303099, was obtained from National Institute of Agrobiological Sciences Genebank, and *Medicago sativa rhizobia, Sinorhizobium meliloti* 1021 (NBRC 14782$^T$), was obtained from National Institute of Technology and Evaluation, and chromosomal DNAs thereof were used as templates for gene amplification.

The aforementioned two kinds of microorganisms were subjected to liquid shaking culture in 5 mL of TY medium (0.5% Bacto Trypton, 0.3% Bacto Yeast extract, 0.04% CaCl$_2$) at 28° C. for 3 days. After the culture, bacterial cells were collected by centrifugation (4° C., 5000×g, 10 min), and chromosomal DNAs were extracted from the bacterial cells according to a conventional method.
(Amplification of Object Gene)

A gene encoding the enzyme of the present invention shown in Table 1 was amplified by a polymerase chain reaction (PCR) using chromosomal DNA of each bacterial cell as a template. Expand High Fidelity PCR System (Roche) was used for the aforementioned PCR. The reaction conditions are shown in Table 2. The conditions for the cloning and expression are shown in Table 3. The sense primers and antisense primers using *Lotus corniculatus rhizobia, Mesorhizobium loti* MAFF303099, and *Medicago sativa rhizobia, Sinorhizobium meliloti* 1021, as templates are shown in SEQ ID NOs: 5 and 6, and SEQ ID NOs: 7 and 8, respectively.

TABLE 1

Proline hydroxylase used for experiment

| Microorganism to be gene source | Strain name | GenBank Protein No. | Putative protein function published | Number of bases | Amino acid residue |
|---|---|---|---|---|---|
| Mesorhizobium loti | MAFF303099 | BAR52605.1 | L-proline 3-hydroxylase | 843 | 280 |
| Sinorhizobium meliloti | NBRC 14782$^T$ | CAC47686.1 | PUTATIVE L-PROLINE 3-HYDROXYLASE PROTEIN | 843 | 280 |

TABLE 2

PCR conditions

| Temperature (° C.) | Time (sec) | Cycle |
|---|---|---|
| 94 | 180 | 1 |
| 94 | 15 | 25 |
| 50 | 10 | |
| 72 | 50 | |
| 72 | 420 | 1 |

TABLE 3

Cloning and expression conditions

| No | Item | | BAB52605.1 (*Mesorhizobium loti*) | CAC47686.1 (*Sinorhizobium meliloti*) |
|---|---|---|---|---|
| 1 | Host Vector | | *Escherichia coli* Rosetta2 (DE3) pET-21d (+) | |
| 2 | Primer | Sense | 5'-TGAATATACCATGGCAACG CGGATATTGGGTGTGGTC-3' (SEQ ID NO: 5) | 5'-TGAATATACCATGGGCACCC ATTTCTTGGGCAAGG-3' (SEQ ID NO: 7) |
| | | Anti-sense | 5'-ATGAATTCAAGCTTATAAG TCATGACCTCGCCAGCAGCAC-3' (SEQ ID NO: 6) | 5'-ATGAATTCAAGCTTGTATGT CATCACCTCGCCACGTTC-3' (SEQ ID NO: 8) |

TABLE 3-continued

Cloning and expression conditions

| No | Item | | BAB52605.1 (Mesorhizobium loti) | CAC47686.1 (Sinorhizobium meliloti) |
|---|---|---|---|---|
| 3 | Restriction enzyme recognition sequence | 5' side<br>3' side | Nco I<br>Hind III | |
| 4 | Culture method (expression) | Pre-culture<br><br>Main culture | inoculation of single colony to LB medium (5 ml) + Amp 100 μg/ml + Cm 34 μg/ml<br>↓<br>culture at 37° C., 200 rpm, 16 hr<br>addition of pre-culture medium (1 ml) to LB medium (100 ml) + Amp 100 μg/ml + Cm 34 μg/ml, and culture at 37° C., 200 rpm to reach O.D.$_{650}$ = 0.5<br>↓<br>addition of IPTG (final concentration 0.1 mM) and culture at 25° C., 100 rpm, 9 hr | |

(Obtainment of Recombinant Plasmid)

The object DNA amplified by PCR was used as insert DNA, and each insert DNA (1 μg) and a vector, pET-21d(+) (1 μg), were cleaved by a reaction using restriction enzymes NcoI and HindIII at 37° C. for 16 hr. The cleavage products were purified by GFX PCR Purification Kit (GE Healthcare), and each insert DNA and vector were ligated by a reaction using DNA Ligation Kit <Mighty Mix> (Takara) at 16° C. for 3 hr. The ligation product was transduced by a heat shock method into *Escherichia coli* JM109 treated with calcium chloride. *Escherichia coli* JM109 carrying each recombinant plasmid was cultured in an LB-A agar medium (1% Bacto Trypton, 0.5% Bacto Yeast extract, 1% NaCl, 1.5% Bacto Agar, 100 μg/mL ampicillin) at 37° C. for 16 hr, and then cultured in an LB-A liquid medium (1% Bacto Trypton, 0.5% Bacto Yeast extract, 1% NaCl, 100 μg/mL ampicillin, 5 mL) at 37° C. for 1.6 hr, after which the plasmid was extracted using QIAprep Spin Miniprep Kit (QIAGEN). The internal base sequence of the extracted plasmid was analyzed by a DNA Sequencer to confirm insertion of desired DNA. The plasmid maps of the produced recombinant plasmids are shown in FIG. 1.

(Expression of Object Gene)

The recombinant plasmids confirmed of insertion of DNA encoding each of BAB52605 protein and CAC47686 protein (to be referred to as pEBAB52605 and pECAC47686, respectively) were transduced by a heat shock method into *Escherichia coli* Rosetta 2 (DE3) treated with calcium chloride, and expressed by the procedures shown in Table 3. That is, the aforementioned *Escherichia coli* was cultured in an LB-AC agar medium (1% Bacto Trypton, 0.5% Bacto Yeast extract, 1% NaCl, 1.5% Bacto Agar, 100 μg/mL ampicillin, 34 μg/mL chloramphenicol) at 37° C. overnight. The single colony grown was inoculated in an LB-AC liquid medium (1% Bacto Trypton, 0.5% Bacto Yeast extract, 1% NaCl, 100 μg/mL ampicillin, 34 μg/mL chloramphenicol, 5 mL), and cultured with shaking at 37° C. and 200 rpm for 16 hr. Thereafter, the aforementioned liquid medium (1 mL) was added to a fresh LB-AC liquid medium (100 mL), and cultured with shaking at 37° C. and 200 rpm. At the time point when O.D.$_{660}$=0.5 was reached, isopropyl-β-d-thiogalactopyranoside (IPTG) was added to a final concentration of 0.1 mM, the mixture was cultured at 25° C. and 100 rpm to induce gene expression. After 9 hr, the cultured cells were collected by centrifugation (4° C., 5000×g, 10 min), and suspended in 20 mM HEPES NaOH buffer (pH 7.5, 5 mL). The aforementioned suspension was disrupted by ultrasonication (3 min), centrifuged (4° C., 20000×g, 30 min), and the supernatant (cell-free extract) was collected.

1-2. Results

By the aforementioned extraction and amplification operation, genes encoding BAB52605 protein and CAC47686 protein were successfully cloned. By the aforementioned recombinant operation and the like, recombinant plasmids containing the aforementioned genes could be produced. The plasmid maps of the obtained recombinant plasmids are shown in FIG. 1. By the transduction operation of the aforementioned recombinant plasmids, transformants having the recombinant plasmids could be produced. By the expression operation of the aforementioned genes by the aforementioned transformants, cell-free extracts containing BAB52605 protein and CAC47686 protein could be respectively obtained. The obtained cell-free extracts were used for the following experiments.

Example 2

2. Hydroxylation Reaction of L-Proline with BAB52605 Protein and CAC47686 Protein 2-1. Method Hydroxylation reaction of L-proline with a cell-free extract containing BAB52605 protein or CAC47686 protein obtained in Example 1 was performed. A reaction solution of the composition shown in Table 4 (hereinafter to be referred to as "standard reaction solution") was prepared, and the reaction was performed with stirring at 30° C. and 170 rpm for 30 min. In addition, as a negative control, a reaction solution obtained by excluding L-proline from the standard reaction solution (hereinafter to be referred to as "Pro-free reaction solution"), a reaction solution free of 2-oxoglutaric acid (2-OG) (hereinafter to be referred to as "2-OG-free reaction solution"), and a reaction solution containing, instead of the cell-free extracts containing BAB52605 protein and CAC47686 protein, a cell-free extract of *Escherichia coli* Rosetta 2 (DE3) free of a vector expressing the aforementioned proteins (hereinafter to be referred to as "nonexpressing reaction solution") were prepared, and the reaction was performed with stirring at 30° C. and 170 rpm for 30 min in the same manner as with the standard reaction solution. After the reaction, according to the procedures shown in FIG. 2, the reaction was quenched and whole amino acids contained in the reaction solution was derivatized using a Marfey's reagent (1-fluoro-2,4-dinitrophenyl-5-L-leucinamide). Thereafter, the reaction solution was filtered with a 0.45 μm filter, and subjected to high performance liquid chromatography (HPLC) analysis. Various conditions of HPLC analysis are shown in Tables 5A and 5B. In addition, for molecular weight measurement of the resultant products, mass spectrometry (MS analysis) of the standard reaction solutions after reaction with a cell-free extract containing BAB52605 protein or CAC47686 protein was performed. According to the procedures shown in FIG. 7, the substance in the reaction solution was purified using an ion exchange column (Waters Oasis HLB 6 cc Extraction Cartridge), dried to solidness under reduced pressure and dissolved in methanol to give an MS analysis sample. The conditions of MS analysis are shown in Table 6.

TABLE 4

Reaction composition

| | |
|---|---|
| L-Proline | 5.0 mM |
| 2-Oxoglutarate | 10 mM |
| L-Ascorbate | 1.0 mM |
| $FeSO_4$ | 0.5 mM |
| HEPES | 100 mM |
| Cell-free extract | 1.0 mg |

Total volume 1 ml 30° C., 30 min, shake

TABLE 5

HPLC analysis conditions (a) Setting

| | |
|---|---|
| Apparatus used | Hitachi high performance liquid chromatograph L-2000 series |
| Analytical column | XDB-C18 (5 μm), 4.6 mm × 150 mm (Agilent) |
| Column temperature | 40° C. |
| Detector | UV 340 nm |
| Eluent | A  50 mM $KH_2PO4/CH_3OH/CH_3CN$ = 90/5/5<br>B  50 mM $KH_2PO4/CH_3OH/CH_3CN$ = 60/5/35<br>C  $CH_3CN/THF/H_2O$ = 60/20/20 |

(b) Pump program

| Time (min) | A (%) | B (%) | C (%) | Flow rate (ml/min) |
|---|---|---|---|---|
| 0.0 | 100 | 0 | 0 | 1.0 |
| 54.0 | 55 | 45 | 0 | |
| 54.1 | 0 | 0 | 100 | |
| 60.0 | 0 | 0 | 100 | |
| 60.1 | 100 | 0 | 0 | |
| 75.0 | 100 | 0 | 0 | |

TABLE 6

MS analysis conditions

| | | |
|---|---|---|
| Apparatus used | LCQ Deca (Thermo Quest) | ESI positive |
| Setting | Sheath Gas Flow Rate | 20 arb |
| | Aux Gas Flow Rate | 20 arb |
| | Spray Voltage | 5 kV |
| | Capillary Temp | 200° C. |
| | Capillary Vortage | 17 V |
| | Tube Lens offset | 5 V |

2-2. Results.

Figure 3:
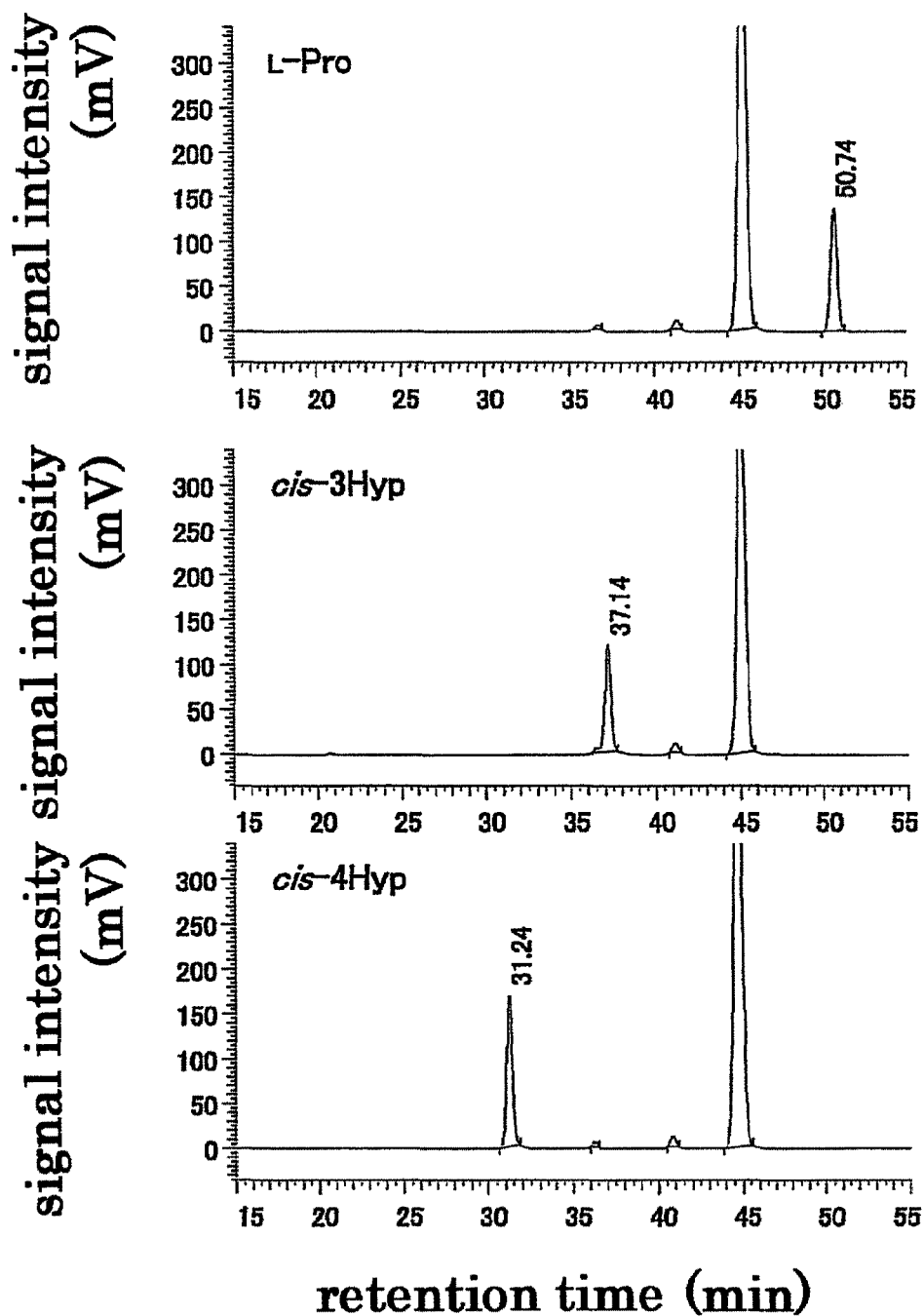
FIG. 3 Graphs showing the results of HPLC analyses of standard samples of L-proline and 4 kinds of isomers of Hyp.
Figure 3:
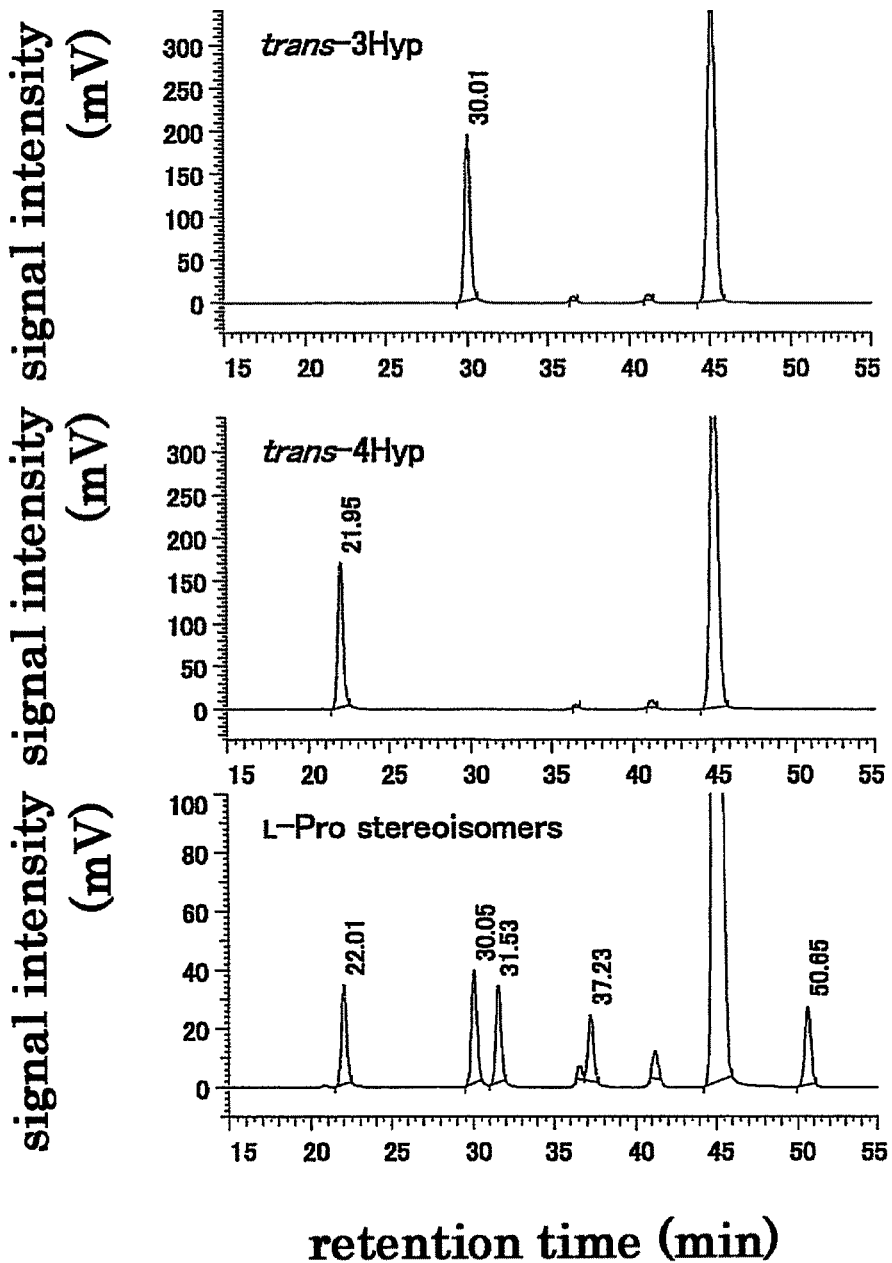

FIG. 3 shows the results of HPLC analysis of standard samples of L-proline and 4 kinds of isomers of Hyp. Since any isomer of Hyp was detected as a separated single peak, the peak substance was identified based on the retention time.

Figure 4:
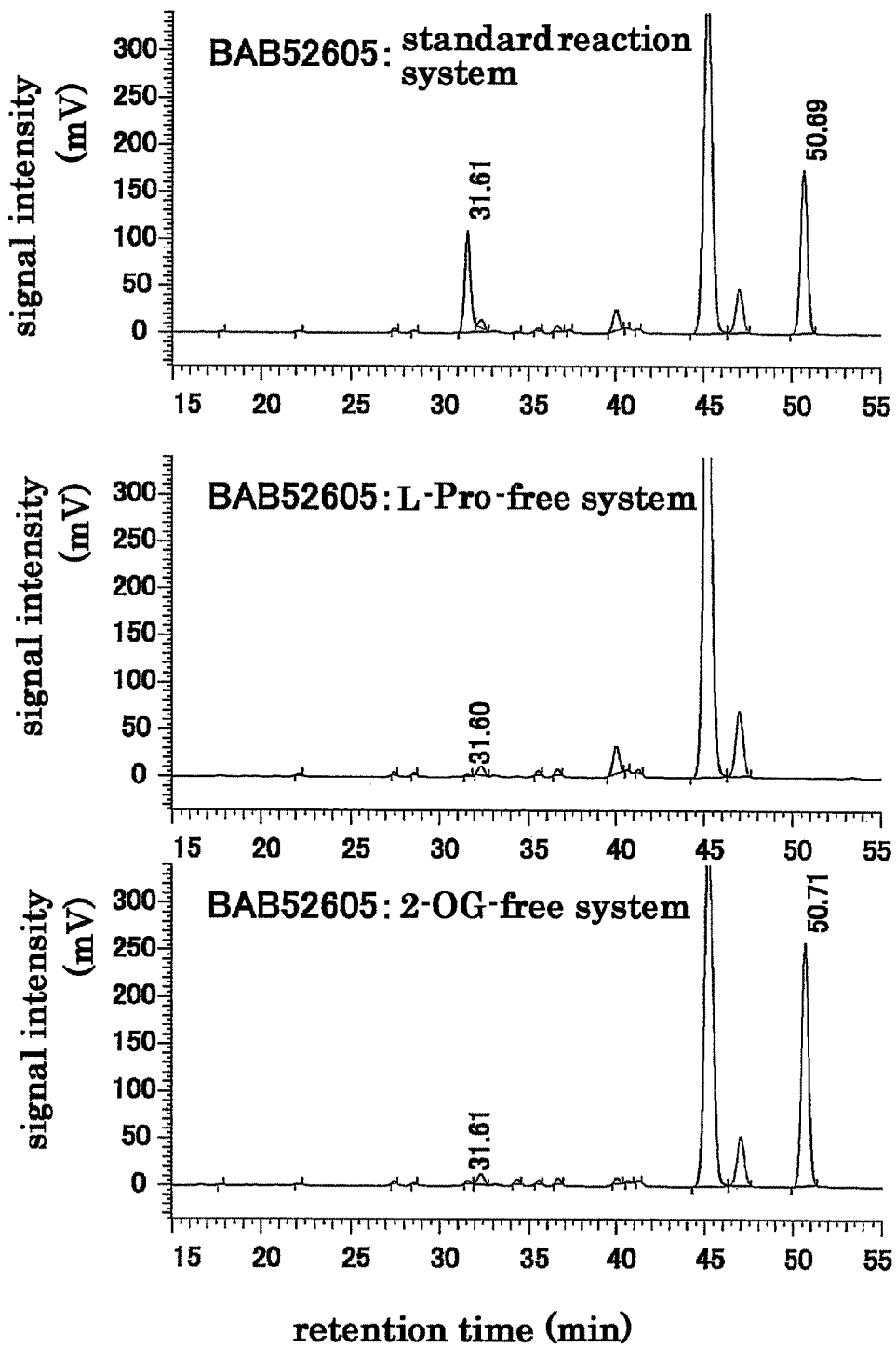
FIG. 4 Graphs showing the results of HPLC analyses of a standard reaction solution from reaction with a cell-free extract containing BAB52605 protein, a Pro-free reaction solution (negative control) and a 2-OG-free reaction solution (negative control).

FIG. 4 shows the results of the HPLC analysis of standard reaction solutions obtained by a reaction with a cell-free extract containing BAB52605 protein, a Pro-free reaction solution (negative control) and a 2-OG-free reaction solution (negative control). While the standard reaction solutions showed a decrease in the peak of L-proline and emergence of peak of cis-4-Hyp, the 2-OG-free reaction solution showed a peak of L-proline alone, and the Pro-free reaction solution showed no peak.

Figure 5:
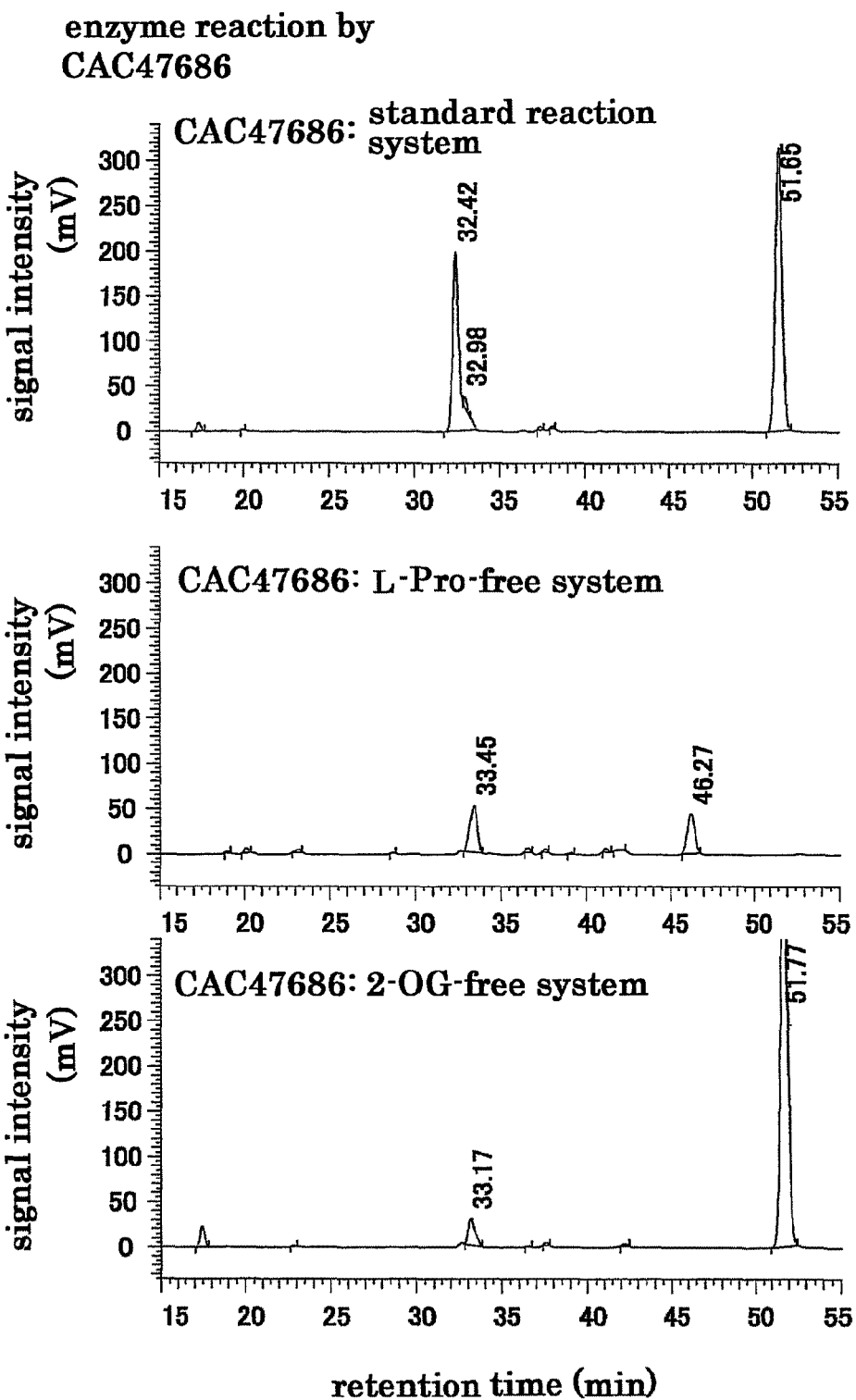
FIG. 5 Graphs showing the results of HPLC analyses of a standard reaction solution from reaction with a cell-free extract containing CAC47686 protein, a Pro-free reaction solution (negative control) and a 2-OG-free reaction solution (negative control).

FIG. 5 shows the results of the HPLC analysis of standard reaction solutions obtained by a reaction with a cell-free extract containing CAC47686 protein, a Pro-free reaction solution (negative control) and a 2-OG-free reaction solution (negative control). Like the results of FIG. 4 using BAB52605 protein, while the standard reaction solutions showed a decrease in the peak of Pro and emergence of peak of cis-4-Hyp, the 2-OG-free reaction solution showed a peak of Pro alone, and the Pro-free reaction solution showed no peak. (Since the small peak in 33 min observed with the 2-OG-free reaction solution was also observed with the Pro-free reaction solution, the peak is considered to be derived from a substance originally contained in the reaction solution, which is not a substrate or a resultant product.)

Figure 6:
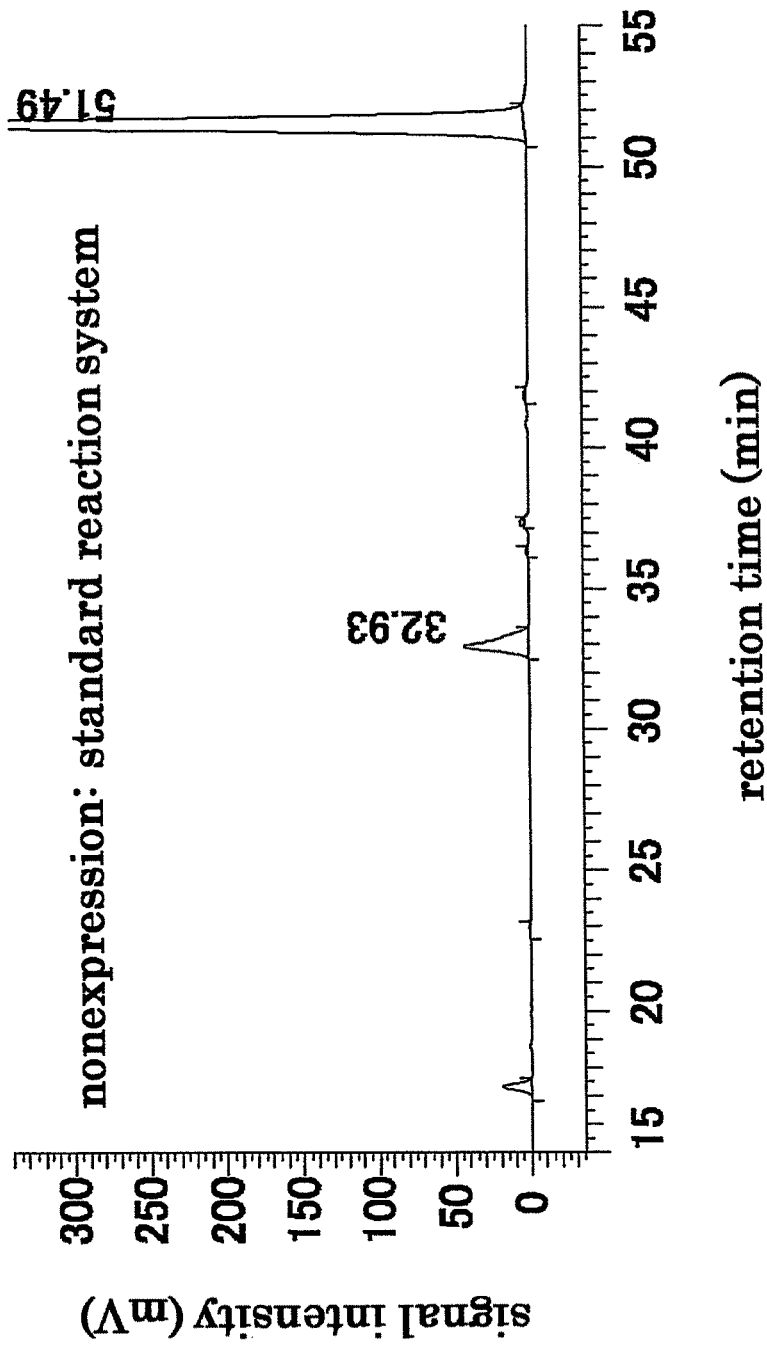
FIG. 6 A graph showing the results of HPLC analysis of a nonexpressing reaction solution (negative control).

FIG. 6 shows the results of the HPLC analysis of nonexpressing reaction solution (negative control). The nonexpressing reaction solution showed only a peak of L-proline.

Figure 8:
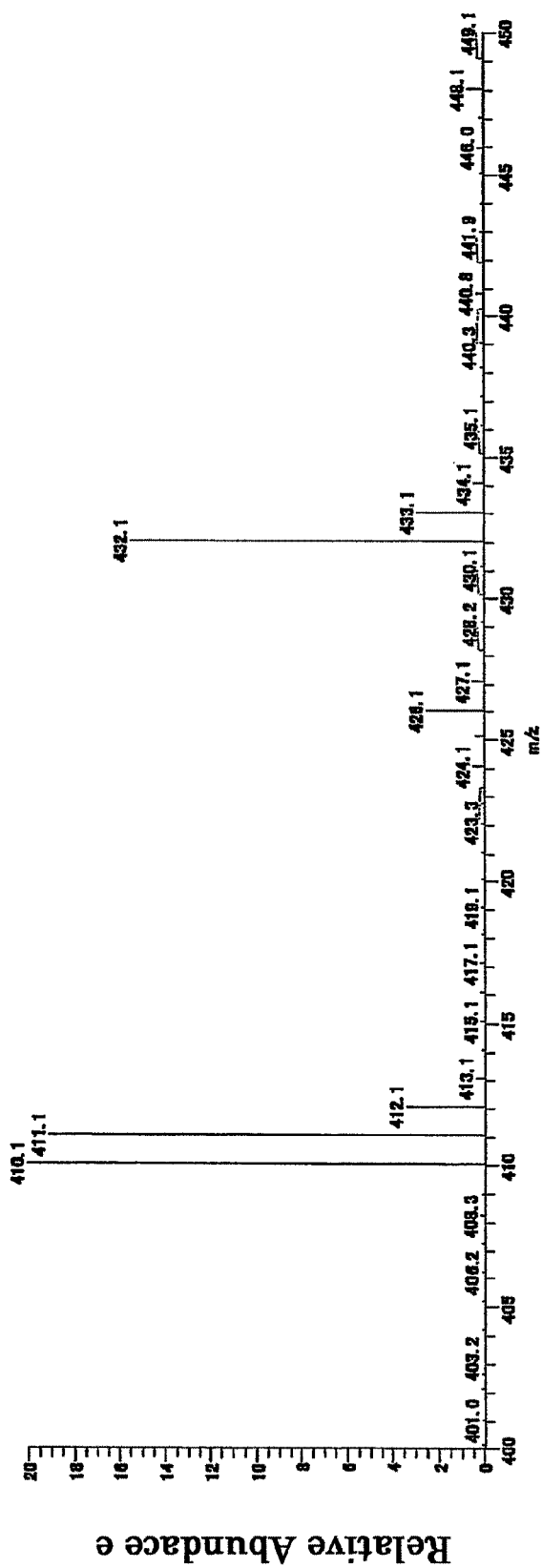
FIG. 8 Graphs showing the results of MS analyses of standard reaction solutions from reaction with cell-free extracts containing BAB52605 protein and CAC47686 protein.
Figure 8:
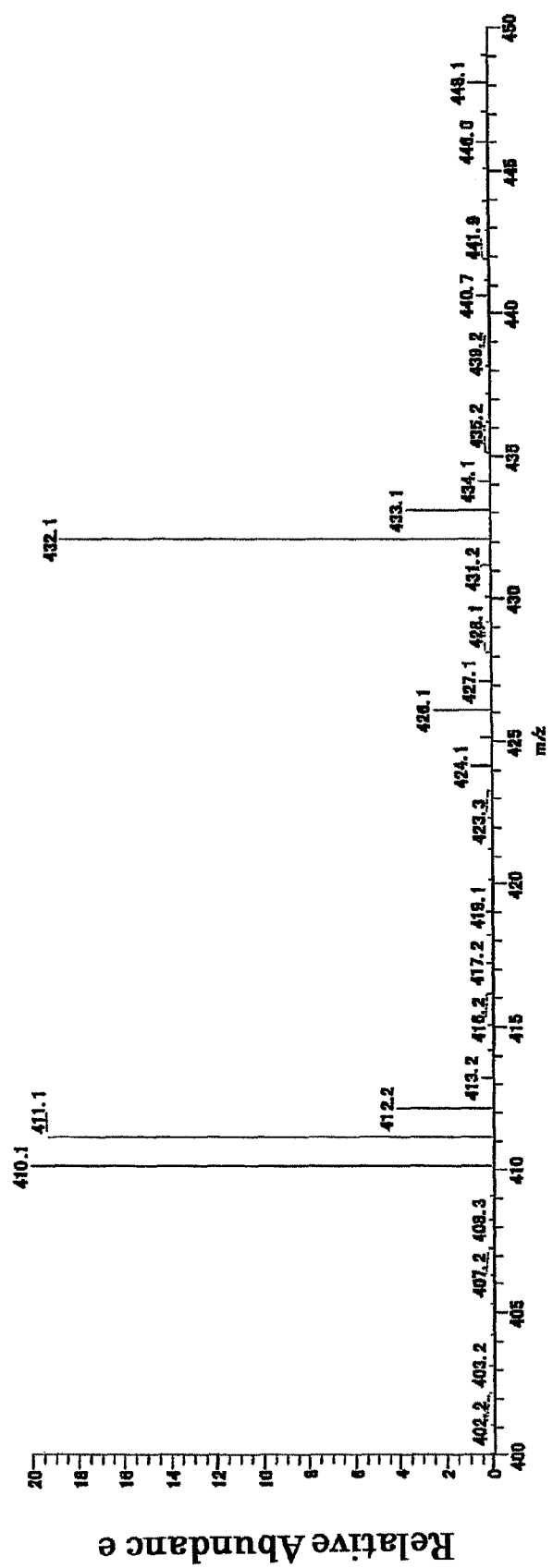

FIG. 8 shows the results of the MS analysis of standard reaction solutions obtained by a reaction with a cell-free extract containing BAB52605 protein (upper panel) or CAC47686 protein (lower panel). In respective analysis results, protonated ion (m/z=426.1) and sodium added ion (m/z=448.1) corresponding to cis-4-Hyp derivatives were detected.

Figure 9:
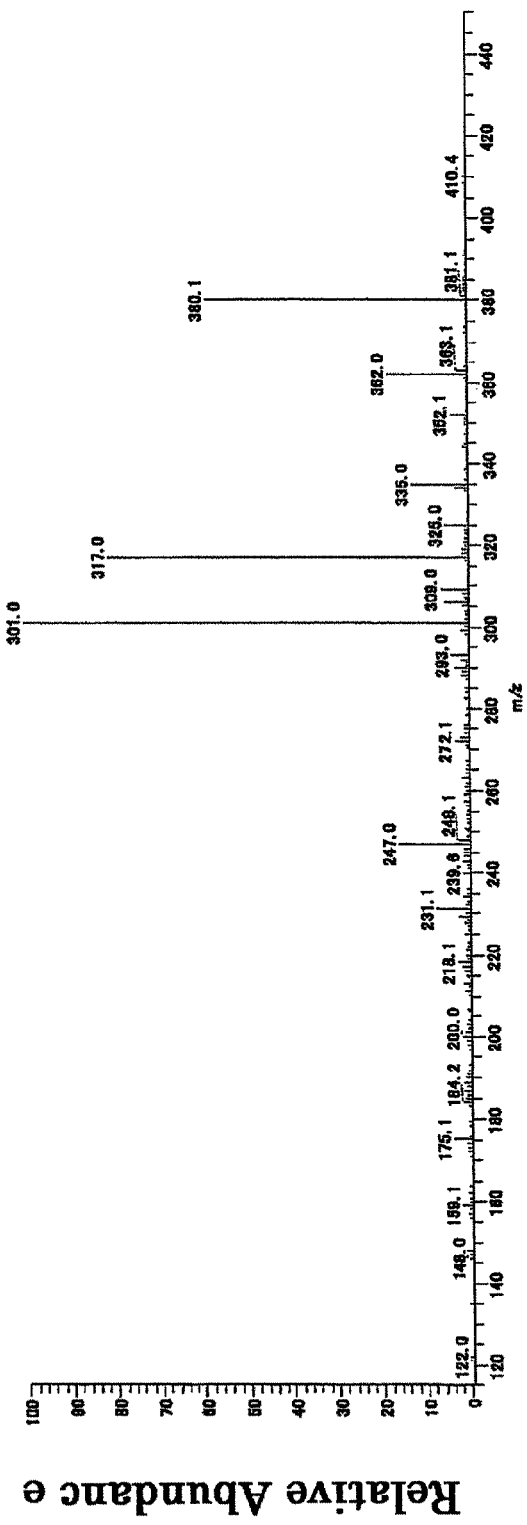
FIG. 9 Graphs showing fragmentation patterns obtained by MS/MS/MS analyses of reaction products in standard reaction solutions from reaction with cell-free extracts containing BAB52605 protein and CAC47686 protein, and a standard sample of cis-4-Hyp.
Figure 9:
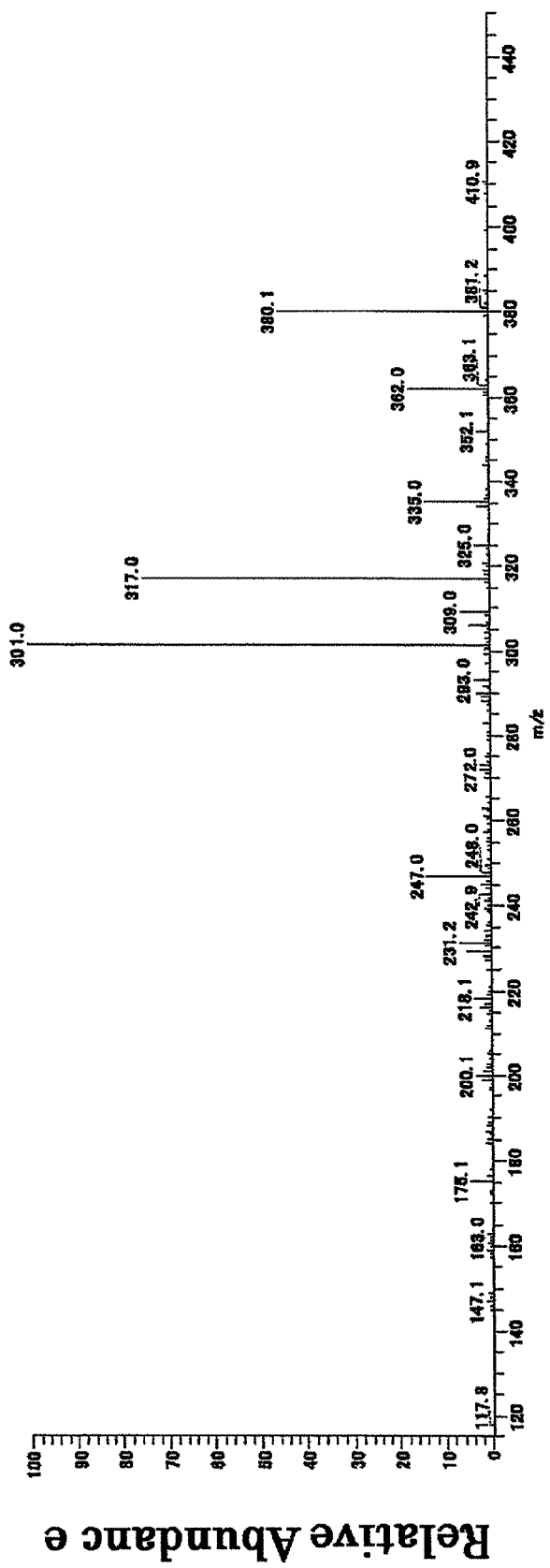
Figure 9:
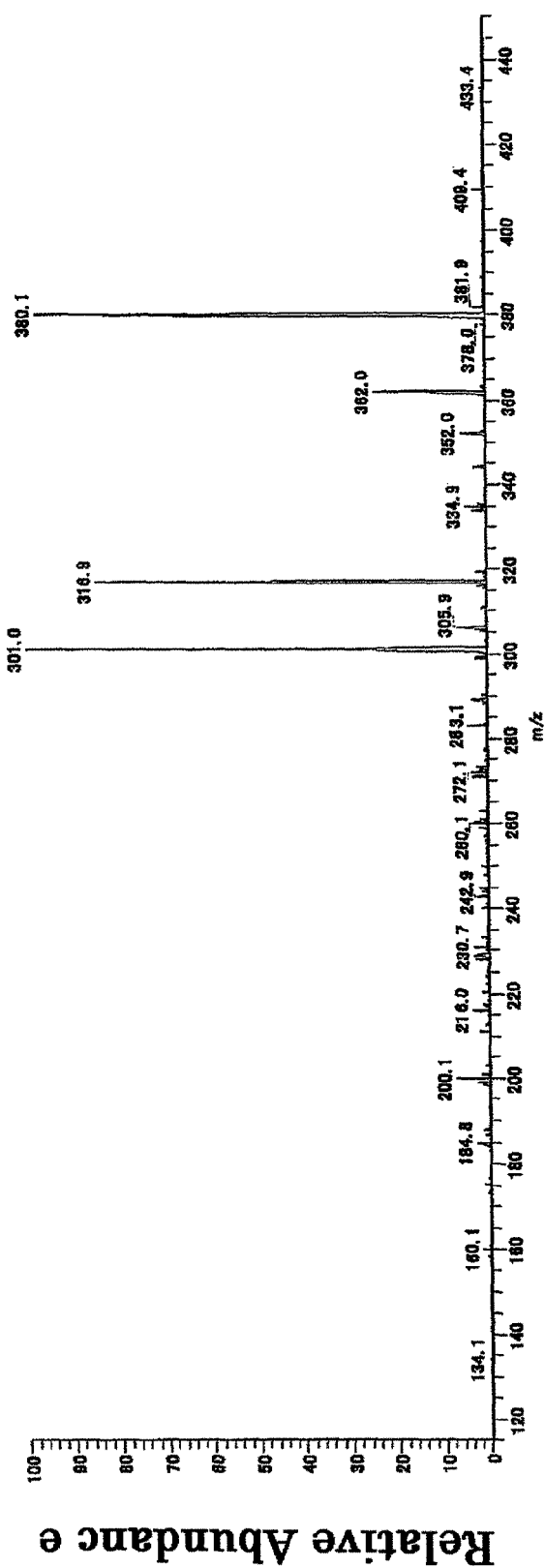

FIG. 9 shows fragmentation patterns obtained by MS/MS/MS analyses of reaction products in standard reaction solutions from reaction with cell-free extracts containing BAB52605 protein (upper panel) and CAC47686 protein (middle panel), and a standard sample of cis-4-Hyp (lower panel). In respective analysis results, a common fragmentation pattern was observed, which confirms that the fragmentation patterns of MS/MS/MS analyses of the reaction products from cell-free extracts containing the aforementioned proteins are the same as the pattern of the cis-4-Hyp standard sample.

From these results, since cis-4-Hyp is produced in the presence of BAB52605 or CAC47686 protein and L-proline, it has been confirmed that the aforementioned proteins are all hydroxygenases that regioselectively and sterically selectively hydroxylate L-proline and produce cis-4-Hyp. The putative protein function disclosed in the databases such as Entrez Protein and the like is "L-proline 3-hydroxylase" for BAB52605 protein and "PUTATIVE L-PROLINE 3-HYDROXYLASE PROTEIN" for CAC47686 protein. However, the results of this experiment confirm that the function of the both proteins mentioned above is L-proline cis-4-hydroxylase and L-proline 3-hydroxylase activity is absent. Moreover, since cis-4-Hyp is produced in the presence of 2-OG in reactions catalyzed by BAB52605 or CAC47686 protein, both the aforementioned proteins were confirmed to be 2-OG dependent dioxygenases that add an oxygen atom between the carbon atom at the 4-position of Pro and a hydrogen atom bonded thereto in the presence of 2-OG.

The invention claimed is:

1. A method of producing cis-4-hydroxy-L-proline, comprising:
   (A) a step of providing L-proline and at least one protein selected from the group consisting of
   (1) the protein consisting of SEQ ID NO: 1 or 2,
   (2) a protein consisting of an amino acid sequence wherein one or several amino acids is/are deleted from, substituted in, or added to the amino acid sequence of SEQ ID NO: 1 or 2, wherein said protein has L-proline cis-4-hydroxylase activity, and
   (3) a protein consisting of an amino acid sequence encoded by a polynucleotide that hybridizes under stringent conditions with the nucleic acid complement of SEQ ID NO: 3 or 4, wherein said protein has L-proline cis-4-hydroxylase activity and, wherein said stringent conditions comprise hybridization overnight in a solution of 6× saline-sodium citrate (SSC) and 0.2% sodium dodecyl sulfate (SDS) at 65° C., washing two times with a solution of 1×SSC and 0.1% SDS at 65° C. for 30 minutes, and washing two times with a solution of 0.2×SSC and 0.1% SDS at 65° C. for 30 minutes, and
   (B) a step of reacting the at least one protein with the L-proline to give cis-4-hydroxyproline.

2. The method of claim 1, wherein the protein is the protein consisting of SEQ ID NO: 1 or 2.

3. The method of claim 1, wherein the protein is a protein consisting of an amino acid sequence wherein one or several amino acids is/are deleted from, substituted in, or added to the amino acid sequence of SEQ ID NO: 1 or 2, wherein said protein has L-proline cis-4-hydroxylase activity.

4. The method of claim 1, wherein the protein is a protein consisting of an amino acid sequence encoded by a polynucleotide that hybridizes under stringent conditions with the nucleic acid complement of SEQ ID NO: 3 or 4, wherein said protein has L-proline cis-4-hydroxylase activity and, wherein said stringent conditions comprise hybridization overnight in a solution of 6× saline-sodium citrate (SSC) and 0.2% sodium dodecyl sulfate (SDS) at 65° C., washing two times with a solution of 1×SSC and 0.1% SDS at 65° C. for 30 minutes, and washing two times with a solution of 0.2×SSC and 0.1% SDS at 65° C. for 30 minutes.

* * * * *